United States Patent
Huang et al.

(10) Patent No.: US 7,742,633 B2
(45) Date of Patent: Jun. 22, 2010

(54) APPARATUS AND METHOD FOR RAPIDLY MEASURING 3-DIMENSIONAL FOOT SIZES FROM MULTI-IMAGES

(76) Inventors: Jung-Tang Huang, 5F., No.7, Lane 10, Sec. 2, Bade Rd., Da-an District, Taipei (TW) 106; Fuko Yu, No.1, Sec. 3, Jhongsiao E. Rd., Da-an District, Taipei (TW) 106

( * ) Notice: Subject to any disclaimer, the term of this patent is extended or adjusted under 35 U.S.C. 154(b) by 1153 days.

(21) Appl. No.: 11/271,709

(22) Filed: Nov. 11, 2005

(65) Prior Publication Data
US 2006/0104503 A1  May 18, 2006

(30) Foreign Application Priority Data
Nov. 18, 2004  (TW) .............................. 93135353 A

(51) Int. Cl.
*G06K 9/00* (2006.01)
*A61B 5/117* (2006.01)
*G01B 7/00* (2006.01)

(52) U.S. Cl. .................... 382/154; 600/592; 702/155

(58) Field of Classification Search ................ 382/100, 382/108, 110, 115, 128, 154, 160; 702/153, 702/155, 159; 600/592
See application file for complete search history.

(56) References Cited

U.S. PATENT DOCUMENTS

| | | | |
|---|---|---|---|
| 6,289,107 B1* | 9/2001 | Borchers et al. | 382/100 |
| 6,373,963 B1* | 4/2002 | Demers et al. | 382/108 |
| 6,377,353 B1* | 4/2002 | Ellis | 356/603 |
| 7,089,152 B2* | 8/2006 | Oda et al. | 702/182 |
| 7,209,586 B2* | 4/2007 | Massen | 382/154 |
| 7,298,889 B2* | 11/2007 | Massen | 382/154 |
| 2002/0048392 A1* | 4/2002 | Kim et al. | 382/128 |
| 2004/0081336 A1* | 4/2004 | Brooks | 382/111 |

* cited by examiner

*Primary Examiner*—Yon Couso

(57) ABSTRACT

An apparatus and method that uses at least six digital cameras to capture images of the foot, can reconstruct the 3D model of the foot rapidly. Users can only wear elastic socks, which have specially coded multicolored stripes or spots, and stands on the transparent plate of a platform. First from two parallel cameras under the transparent plate, the 3D contour about the sole of the foot can be computed and reconstructed through stereosis algorithm. Similarly, from the other four cameras at least around the upper part of the foot, four or more curved surfaces are combined to reconstruct 3D contour of the upper portion of the foot. Combining the bottom contours and upper contours of the foot the complete 3D foot model can be obtained.

3 Claims, 6 Drawing Sheets

APPARATUS AND METHOD FOR RAPIDLY MEASURING 3-DIMENSIONAL FOOT SIZES FROM MULTI-IMAGES

TECHNICAL FIELD

The invention related to the field of foot measurement, and more specifically, an apparatus for and method of automating the 3-D (three dimensional) contour measurement of a foot using images captured by cameras on the foot worn a special coded sock. The measurements would be used to choose the fitting shoes or to make the suitable ones.

BACKGROUND

There are some apparatuses used to measure the foot dimension. The Yeti™ 3D Foot Scanner as shown in FIG. 1, sold by the Vorum research corporation in U.S.A. There are eight high resolution cameras and four laser projectors used to define the foot dimensions. The advantage of the apparatus is it can rapidly get the foot measurements within four seconds and the tolerance is within 0.5 mm. The disadvantage of the apparatus is too expensive and it's suitable for research lab to use. Because the hardware and the software of the apparatus cost more than one hundred thousand US$ dollars, it's not suitable for retail sales or shops or mail order to be used to help consumers finding the suitable shoes.

Therefore, the present invention is directed to disclose a new low-cost apparatus of 3-D foot contour measurement to satisfy the consumer with finding suitable shoes in the retail sales or shops or via mail order.

SUMMARY

In one embodiment, the invention relates to a system for measuring 3-D contour of a person's foot. The user wears socks that are printed with specific coded patterns. The neighboring imaging devices capture the images of features on the socks, which are regarded as the corresponding points of stereosis and can be used to reconstruct the 3-D model of the foot.

In another embodiment, the invention relates to a system for measuring 3-D contour of a person's foot. The invention is to create the three dimensional model of the foot by operating the program like OpenGL and transferring the 3-D surface of the foot to the CAD/CAM software, such as Solidworks or Pro E. It could be used to help the users choosing or making the suitable shoes.

BRIEF DESCRIPTION OF THE DRAWINGS

The accompanying drawings, which are incorporated in and constitute a part of this specification, illustrate a system consistent with the invention and, together with the description, serve to explain the principles of the invention.

DETAILED DESCRIPTION OF PREFERRED EMBODIMENTS

Figure 1:
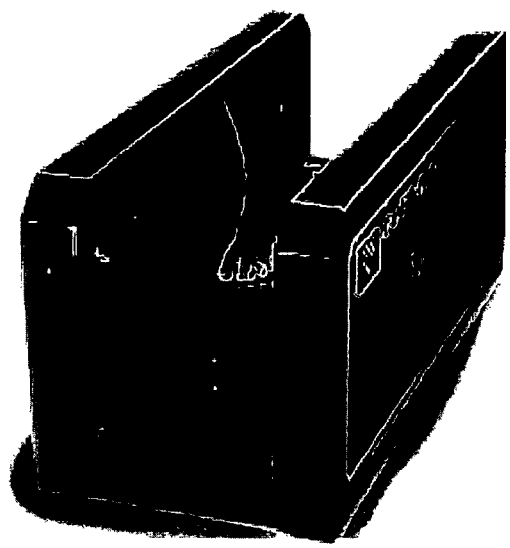
FIG. 1 is an illustration of the prior equipment named as Yeti™ 3D Foot Scanner
Figure 2:
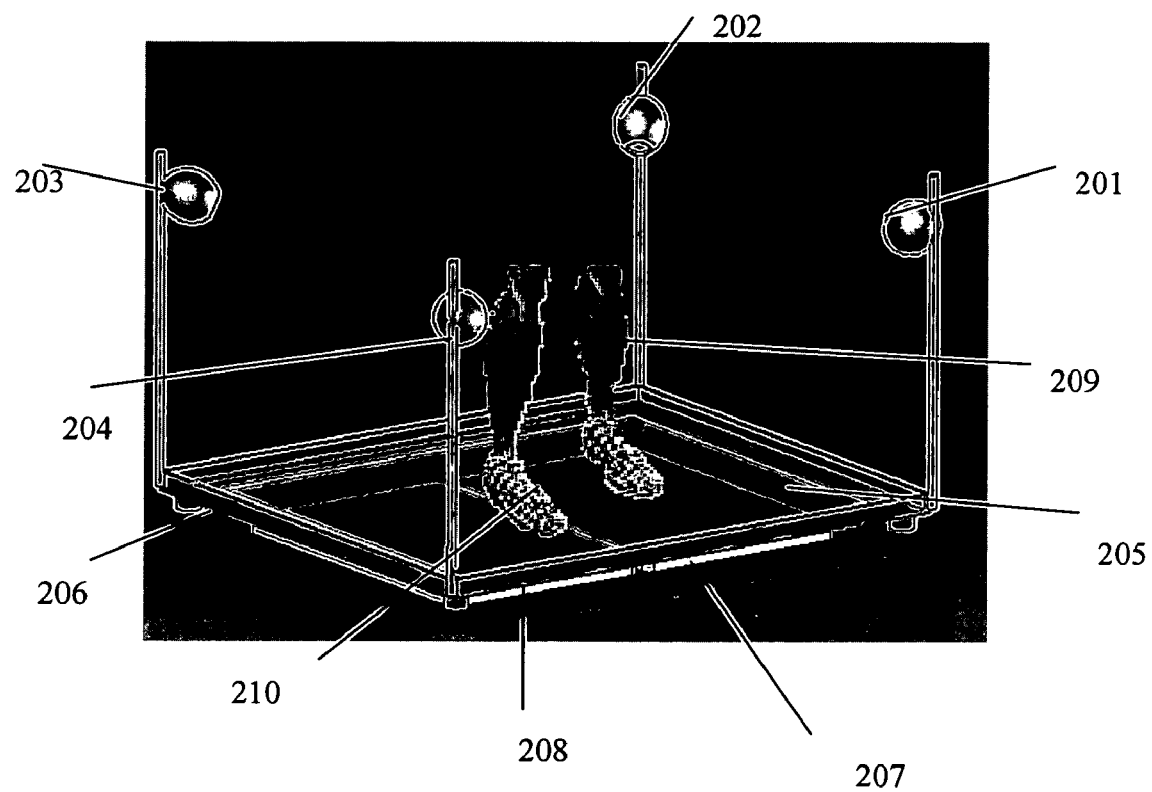
FIG. 2 is a system diagram of hardware elements within the experiment apparatus in an exemplary embodiment consistent with the present invention.

Referring now to the drawings, and in particular to FIG. 2, one embodiment of a measuring system used for measuring the foot of a person incorporating features of this invention is indicated. The passive light sources are employed in the system and in the surrounding of the apparatus. The apparatus includes at least four Charge Coupled Device (CCD) cameras or Complementary Metal-Oxide Semiconductor (CMOS) cameras that are called cameras as following from 201 to 204, the tempered glass 205, the frames 206 and the scanners or cameras 207 & 208 under the tempered glass 205. If the resolutions of the cameras or the scanners are higher, the precision of the 3-D foot-surface-model reconstructed by the apparatus will be better.

In general, the cameras need to be calibrated before using more than one camera to create the stereograph. After calibration process, we can obtain the parameters of the lens in the cameras, including the focal length, aberration, and distortion, etc. Furthermore, the posture of the cameras, including the relative translational displacement and the relative rotational angles of the cameras in the absolute coordinates, are obtained by the calibration process. According to the methods of the stereosis, all images captured by the adjacent cameras could be used to reconstruct the dimensions of the foot surface model.

Stereosis analysis process has a procedure as following. First it is to find out the same corresponding points in the images captured by two adjacent cameras. Then, the depth value (Z-axis) of the corresponding point in the absolute coordinate would be calculated by the triangulation and the X value and Y value could be obtained by the same way. The method and theory could be referred to a common textbook about computer vision, for example "Forsyth & Ponce, Computer vision A modern approach, Prentice Hall, 2003". The textbook would give details which won't be explained furthermore in the present invention.

In order to implement the stereosis process, it needs enough feature points on the foot surface that could be recognized by the adjacent cameras. The same feature points on two images captured by two cameras could be identified. In order to improve the positional resolution between actual foot and the model created by the stereosis, the quantities or densities of feature points distributed on the foot should be enough. The invention discloses a simple and low-cost method to provide enough numbers of feature points on the foot. That means the user can wear an elastic sock printed with a lot of special encoded patterns. Thus it is easy to find all the corresponding points or feature points on two images captured by two adjacent cameras and to create an accurate 3-D foot surface model.

Figure 5:
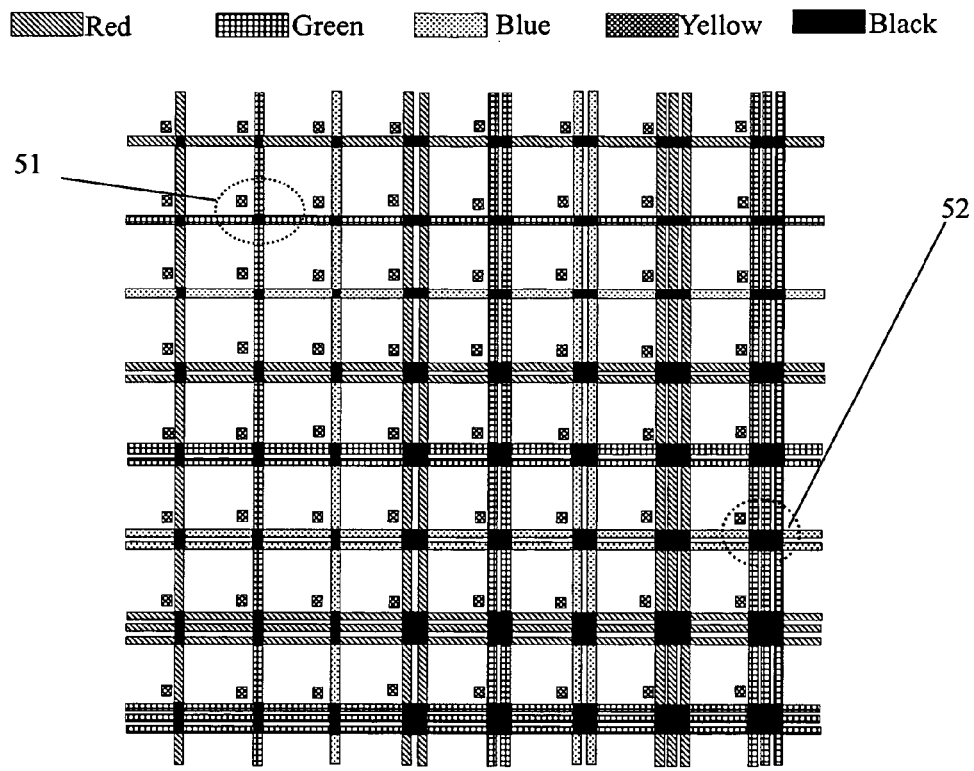
FIG. 5 is an illustration of the special designed codes in an exemplary embodiment consistent with the present invention.

Referring to FIG. 5, one embodiment of the invention discloses a special encoding pattern that three color lines, including red, green and blue, black point and yellow points are used as the feature codes. The black point indicates the intersection point of the different lines and the yellow point is in the left-up corner with respect to black one. The basic concept in the invention is that digital codes would not be influenced by the variation of the foot surface and the view angles of the cameras. Therefore, the same digital codes between two adjacent cameras would be explicit and easy to match without ambiguity for being regarded as corresponding points or conjugate pairs of stereosis algorithm.

It has to be emphasized that there are many methods to encode the feature points. The feature points could be identified by line numbers, color, point numbers, shape or other varied digital properties that are sufficient to be recognized and decoded while matching the corresponding points on the foot. FIG. 5 is one of the embodiment examples. The prior art uses corresponding points projected by the laser projector. Its cost is too expensive for common shoe store to use. Therefore, this invention provides a sock with special codes to substitute the expensive laser projector.

Figure 3:
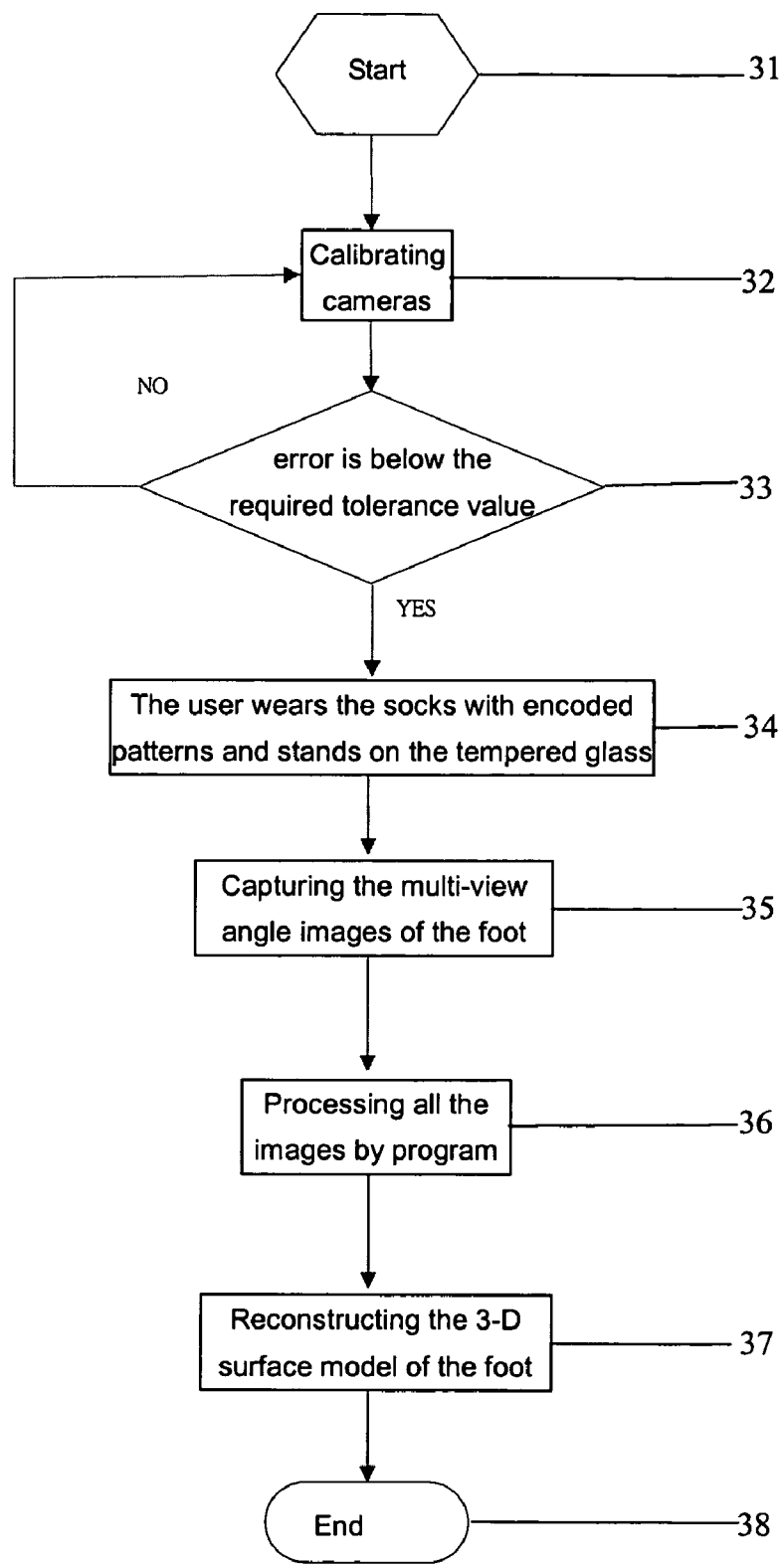
FIG. 3 is a flow chart of the operation system in an exemplary embodiment consistent with the present invention.

The flow chart of the program for the invention is shown in FIG. 3. While the program is executed 31, cameras have to be calibrated 32 until the error is below the required tolerance value 33. Then the user 209 wears the socks 210 with encoded patterns as shown in FIG. 2 and stands on the tempered glass 205. The distance between two feet is kept about the same as the width of the shoulder. When the user 29 stands on the tempered glass steadily, the system will implement the step 35 to start the cameras 201, 202, 203, 204 and the scanners or cameras 207, 208, such that the images of the foot with a coded sock would be captured into the computer and the program 36 would process all the images.

Figure 4:
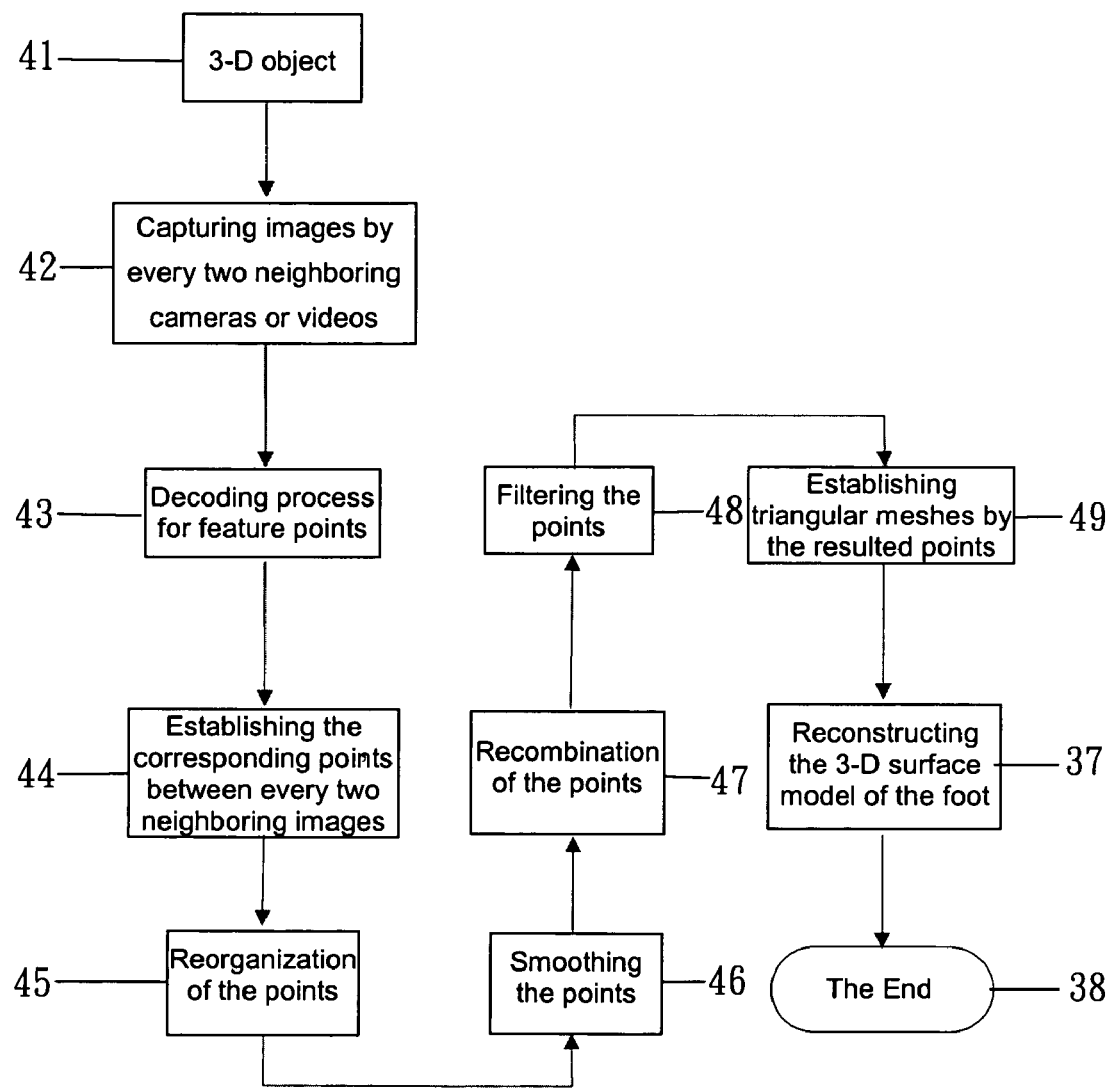
FIG. 4 is an image process flow chart in an exemplary embodiment consistent with the present invention.

Step 36 is described in detail in FIG. 4. The 3-D object 41 is the user's foot 29. Every two neighboring images are captured by cameras 21, 22, 23, 24 in step 42. The decoding process for feature points 43 has to be run first and the corresponding points between every two neighboring images would be established 44. Then the corresponding points are transformed into the 3-D position point data of the foot. In order to decrease the dimensional error, the cluster of 3-D position point data of the foot would be processed with the following steps, including reorganization 45, smoothing 46, recombination 47 and filtering 48. The resulted points would be used to establish triangular meshes 49 and reconstruct the 3-D surface model 37. After finishing all the processes described above, the final process is to close the program 38.

In summary, the present invention would provide a method for user to create a 3-D surface model of his foot by using multi-view angle cameras, and wearing a thin and elastic sock printed with specially encoded color stripe or points of difference size. Creating the 3-D surface model of foot in the computer could help user to find suitable shoes in a very short time in the shoe store. Or the model data can be transferred to CAD/CAM software to make a pair of customized shoes for specific users. Furthermore, the 3-D surface models of the foot could be regarded as an identification of the user's foot, or a record of foot variation with time, and a virtual foot for buying shoes on the internet or via mail-order.

EMBODIMENT EXAMPLE

The user stands erectly on the measurement platform. The structure of the measurement platform is described in FIG. 2, in which four cameras capture images into the computer. The images would be processed by the system program and the feature points in the images would be decoded to obtain the RGB stripe codes, and then find out the conjugate pair or corresponding points. Use triangular measurement to calculate the world coordinate positions of the corresponding points in two adjacent cameras. After getting the cluster of coordinate points, the post-process for the points can be run as the following steps:

Reorganization of the points would redistribute the points more uniformly that is useful to create the surface.

1. Smoothing: there is noise for the point data, especially the points near the shape geometry with large curvature. This step will remove the noise effectively.

2. Recombination: recombining the points along the direction of the boundary would be useful to blend two adjacent curved surfaces.

3. Filtering: filtering the additional points in the images would avoid the errors in the process of creating curved surfaces.

After finishing the process described above, the triangular meshes could be created by the point data and combination of the meshes would be formed as a 3-D surface model of the foot.

The method to set up the measurement equipment by using the cameras 201, 202, 203, 204 and the platform 206 is shown in FIG. 2. The tempered glass 205 is put and fixed on the platform 206. The user 209 wears a sock 210 printed with special designed codes and stands erectly on the platform that at least four cameras 201, 202, 203, 204 set around the foot. There are also two scanners 207, 208 or two cameras (not shown) set under the tempered glass 205.

Figure 6:
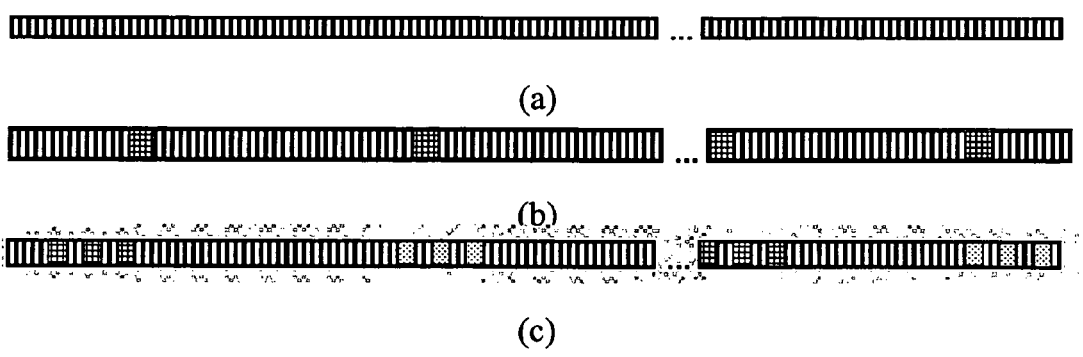
FIG. 6 is an illustration of the RGB bar code in an exemplary embodiment consistent with the present invention.

The method to encode the feature points is shown in FIG. 5. The codes consist of red lines, green lines, and blue lines with different width and several yellow points and black points. First, the center coordinates of the yellow and black points are calculated. The black point is the circle center and the distance between black point and yellow point is the radius of the circle. Along the circle for 360 degree clockwise or counter-clockwise, the RGB value is captured on the circular position at every degree. The direction from circle center to the center of the yellow point is set as the beginning angle. The RGB value of the red color is (255, 0, 0), the green is (0, 255, 0) and the blue is (0, 0, 255). They are used to identify the color of the pixel. The series of RGB values are the codes to identify the corresponding points in the 3-D space. The sketch of the RGB series codes are shown as FIG. 6. The RGB code with no color captured is shown as FIG. 6(a) and the RGB codes with captured color at the point 51 and the point 52 shown in FIGS. 6(b) and (c). The points in two adjacent images with the same RGB series codes are regarded as conjugate pair or corresponding points.

Figure 7:
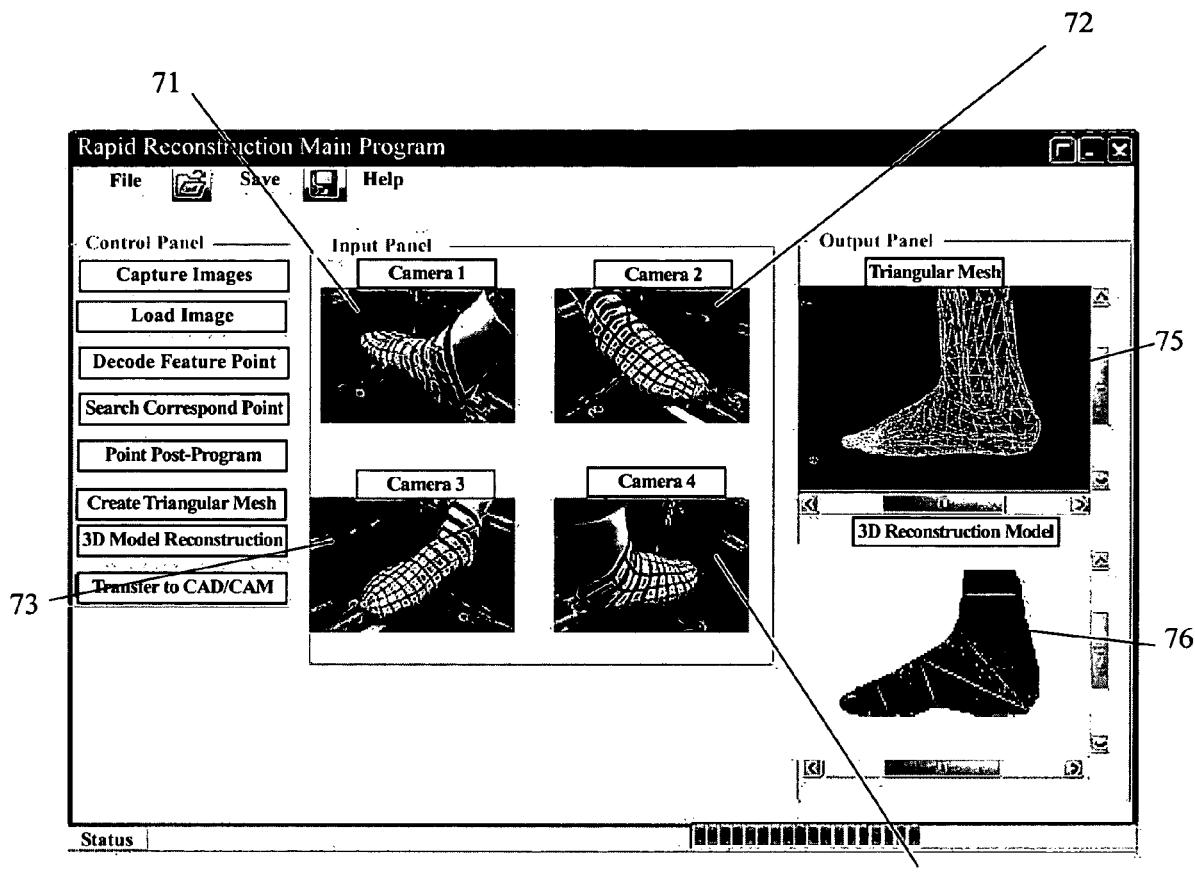
FIG. 7 is an illustration of the main window of the interface in an exemplary embodiment consistent with the present invention.
Figure 8:
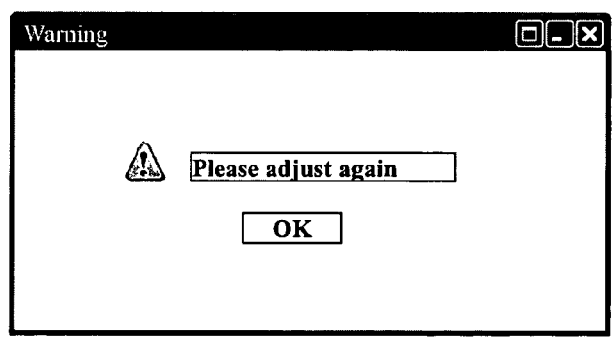
FIG. 8 is an illustration of the warning window of the program in an exemplary embodiment consistent with the present invention.

The interface of the program disclosed in the invention is shown as FIG. 7. The images 71, 72, 73, 74 are captured from the camera 1, 2, 3, and 4. After implementing the processes shown in FIG. 3 and FIG. 4, the 3-D meshes 75 could be created and the 3-D surface model 76 could be established by combination of the meshes.

Figure 9:
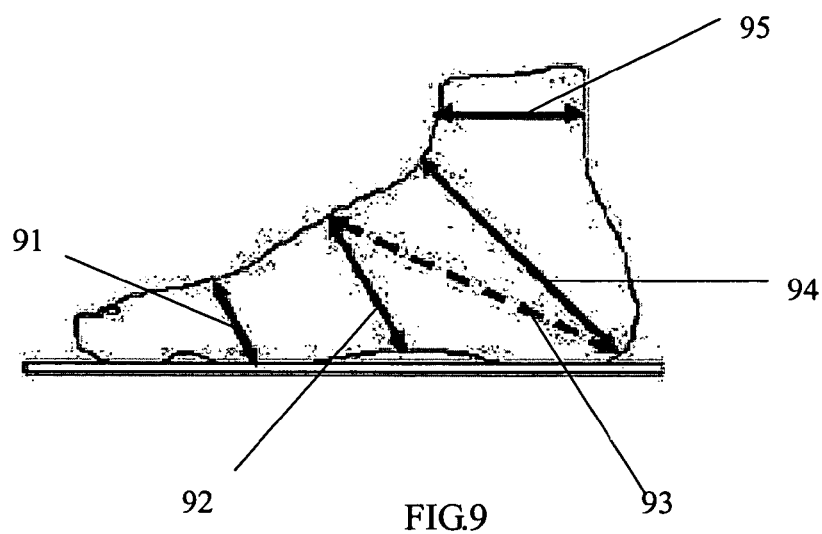
FIG. 9 is an illustration of the measurement of the foot contour dimensions in an exemplary embodiment consistent with the present invention.

The 3-D surface model of foot created by the invention could be used to measure some parameters for making suitable shoes of specific users afterward. The measured dimensions of the foot are illustrated in FIG. 9. The circumference measurement of the foot includes the toes girth 91, the waist-line girth 92, the short heel girth 93, long heel girth 94 and the ankle girth 95, etc.

Figure 10:
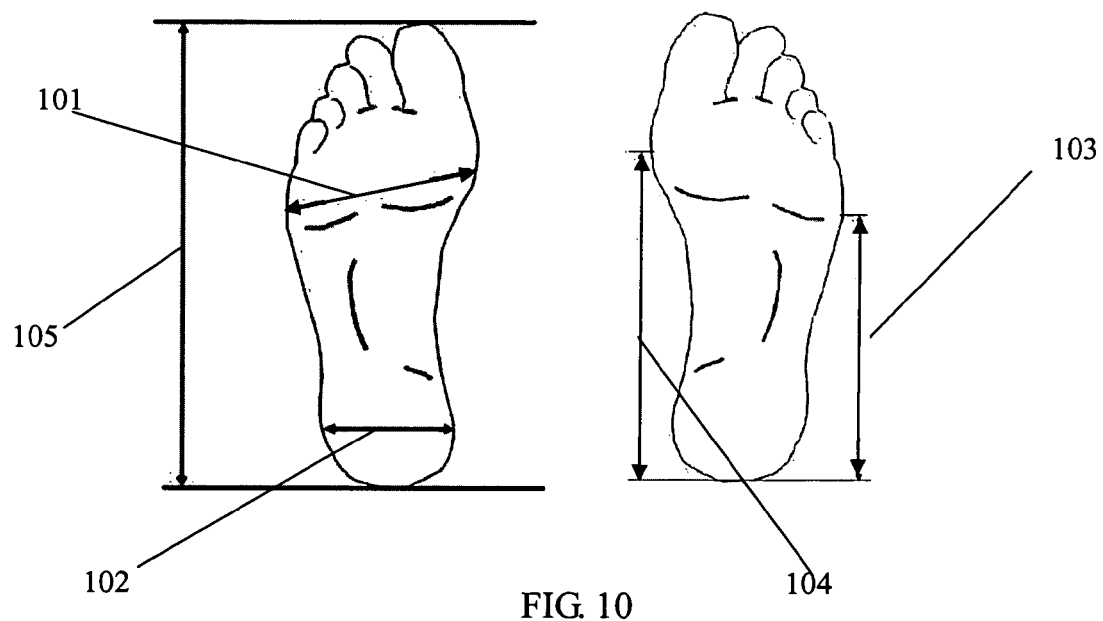
FIG. 10 is an illustration of the measurement of the foot length dimensions in an exemplary embodiment consistent with the present invention.

The length measurements of the foot shown in FIG. 10 include the foot breadth 101 from the inside bulge to the outside one on the metatarsus, the heel breadth 102 measured the shortest distance, the inside fold distance 103 that is from the inside bulge to the heel, the outside fold distance 104 that is from the outside bulge to the heel, and the foot length 105 that is the longest distance of the foot.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method for reconstructing and measuring the three dimensional surface model of a foot, based on an apparatus comprising with one computer, one display device, at least six image capture devices connected with the computer and installed on the platform and geometrically calibrated, and a program implemented in the computer to capture images and reconstruct the 3D surface model, the method comprising:

wearing a thin and elastic sock printed with digitized codes on the foot of a person;

placing the foot of the person on the transparent plate of the platform;

using two image capture devices under the transparent plate and other at least four ones around the foot above the platform to capture the images of the foot from the multi-view angles under and above the foot;

finding the same digitized codes as corresponding points for stereosis in every two images captured by the adjacent image capturing devices;

calibrating the world coordinate positions of the corresponding points by using stereosis algorithms based on the calibration parameters of the image capture device; and reconstructing the three dimensional surface model and dimensions of the person's foot.

2. The method of claim 1, wherein digitized codes consist of different color stripes or points with different size or shape designed specifically for being decoded and analyzed as corresponding points for stereosis.

3. The method of claim 1, wherein the three dimensional surface model and dimensions of the person's foot are further transferred into the database of shoes for recommending the person to select a properly sized pair of shoes or to make a pair of custom shoes accordingly.

* * * * *